United States Patent [19]

Gottlieb

[11] 4,191,751
[45] Mar. 4, 1980

[54] METHOD FOR PROMOTING GROWTH OF NEW CONNECTIVE TISSUE OVER SURFACE WOUNDS

[76] Inventor: Sheldon K. Gottlieb, 8708 Wandering Trail Dr., Potomac, Md. 20854

[21] Appl. No.: 857,526

[22] Filed: Dec. 5, 1977

Related U.S. Application Data

[63] Continuation-in-part of Ser. No. 764,229, Jan. 31, 1977, Pat. No. 4,061,731, Continuation-in-part of Ser. No. 576,858, Jun. 4, 1975, Pat. No. 4,006,220.

[51] Int. Cl.$^2$ .................. A61K 37/12; A61K 31/195
[52] U.S. Cl. ..................................... 424/177; 424/319
[58] Field of Search ........................................ 424/177

[56] References Cited

U.S. PATENT DOCUMENTS

| | | | |
|---|---|---|---|
| 3,325,366 | 6/1967 | Blaug et al. | 424/28 |
| 3,767,784 | 10/1973 | Gluck | 424/28 |

OTHER PUBLICATIONS

Miyata et al.—Chem. Abst. vol. 78, (1973), p. 7817r.
Wilde et al.—Chem. Abst. vol. 76, (1972), p. 94779e.

*Primary Examiner*—Sam Rosen
*Attorney, Agent, or Firm*—Schwartz & Weinrieb

[57] ABSTRACT

Method for promoting the growth of new connective tissue over a surface wound wherein at least a portion of the epithelium has been damaged or removed. The method comprises coating the wound with a composition consisting essentially of a connective tissue promoting agent selected from the group consisting of: (1) pulverized absorbable gelatin sponge, (2) aminocaproic acid, (3) a compound of the formula $4NH_2CH_2(CH_2)_4COOH \cdot CaX_2$ wherein X is chloride or bromide, or (4) mixtures thereof, said composition being present in an amount sufficient to produce new connective tissue over the surface wound. The process is particularly useful for treating both contaminated and uncontaminated, denuded, ulcerated, and/or burned tissue.

10 Claims, No Drawings

METHOD FOR PROMOTING GROWTH OF NEW CONNECTIVE TISSUE OVER SURFACE WOUNDS

This application is a continuation-in-part of my copending application, Ser. No. 764,229, filed Jan. 31, 1977, now U.S. Pat. No. 4,061,731 said application being a continuation-in-part application of my copending application Ser. No. 576,858, filed June 4, 1975, now U.S. Pat. No. 4,006,220.

BACKGROUND OF THE INVENTION

This invention relates to a method for promoting the growth of new connective tissue over a surface wound, and more particularly to a method that encourages the formation of new collagen as a part of the healing process while at the same time providing a temporary covering layer for said surface wound to protect the same against infection and reduce the likelihood of an electrolyte imbalance.

In the past numerous methods have been employed to protect denuded, ulcerated and/or burned tissue. Most of these methods have involved grafting techniques as well as using temporary biological dressings, e.g., amniotic membrane, but these methods fail to take advantage of the natural healing phenomena that is present in this invention.

OBJECTS OF THE INVENTION

It is a significant object of the present invention to provide a method that is useful for the repair of denuded, ulcerated, and burned tissue as well as provide a protective cover therefor to protect the surface wound against infection, and reduce the likelihood of an electrolyte imbalance.

It is a further object of the present invention to provide a simple and efficient process that is capable of protecting the wounded tissue during the healing process.

A still further object of the present invention is the provision of a simple and efficient process capable of enhancing tissue healing in a shorter period of time by the stabilization of fibrin which regulates formation of new collagen.

The invention will be better understood and objects other than those set forth herein will become apparent when consideration is given to the following detailed description and the illustrative embodiments discussed herein.

BRIEF SUMMARY OF THE INVENTION

Briefly, the present invention relates to a method for promoting the growth of new connective tissue over a surface wound wherein at least a portion of the epithelium has been damaged or removed which comprises coating the wound with a composition consisting essentially of a connective tissue growth-promoting agent selected from the group consisting of: (1) pulverized absorbable gelatin sponge, (2) aminocaproic acid, (3) a compound of the formula $4NH_2CH_2(CH_2)_4COOH.CaX_2$ wherein X is chloride or bromide, or (4) mixtures thereof. The composition is present in an amount sufficient to stimulate the production of new connective tissue over the surface wound.

DETAILED DESCRIPTION OF THE INVENTION

The process of the present invention is particularly useful for promoting the growth of new connective tissue over various types of surface wounds including those produced from mechanical trauma, hot oil or water burns, chemical burns, and fire burns. The process is particularly useful in treating denuded and ulcerated tissue, e.g., in diabetes mellitis wherein at least a portion of the epithelium has been damaged or removed. The process is also useful wherein epithelium has been removed from a given surface by surgical means, e.g., punch biopsy, surgical excision.

The compositions that are used in the practice of this invention are used in combination with human blood plasma. The plasma is preferably of human origin and preferably from the same patient being treated in accordance with the process of this invention. The plasma can be initially admixed with the composition, or the blood containing plasma can be permitted to flow into the site of the surface wound where at least a portion of the epithelium has been damaged or lost.

As noted hereinbefore, the compositions used in the process of this invention contain either pulverized absorbable gelatin sponge or aminocaproic acid or the combination of these two materials. Thus, the compositions generally contain between about 5 and 50 mg., preferably between about 30 and 40 mg., of pulverized absorbable gelatin sponge which is desirably proteolytically digestable. The composition also contains up to 75 mg., generally between about 12.5 to 75 mg. and preferably between about 30 and 40 mg. of aminocaproic acid which is preferably epsilon aminocaproic acid or the aminocaproic acid compounds as defined hereinbefore. The amounts set forth herein for both said sponge and aminocaproic acid are for each maximum of 0.5 cc and preferably for each 0.3 to 0.5 cc. of plasma introduced into said cavity. As an optional ingredient, finely divided collagen may also be employed in an amount effective to promote the build-up of new connective tissue or collagen and is generally present in an amount between 5 and 50 mg., and preferably between 20 and 30 mg. for each maximum of 0.5 cc. of plasma introduced over the surface wound.

The compositions as defined hereinbefore are particulary useful when applied to uncontaminated, denuded, ulcerated and/or burned tissue. However, contaminated tissue can also be treated with the process of this invention provided that the surface wound is treated with the appropriate antibiotic and/or germicidal agent, either prior to treatment with the aforementioned composition or said antibiotic and/or germicidal agent(s) may be incorporated into the compositions used in the practice of this invention.

Conventional antibiotics that can be incorporated into the process of this invention include Polymixin B, Bacitracin, Neomycin and Gentamycin.

The amount of connective tissue growth-promoting agents used in combination with plasma and applied over the surface wound is dependent upon several factors including the particular connective tissue promoting agent employed, and the size of the denuded, ulcerated and/or burned area as well as the depth of any depression caused by the loss or damage of epithelium in the surface wound area, but, in any event, the amount employed is sufficient to promote the growth of new connective tissue over the surface wound. Generally, the compositions are applied in an amount sufficient to provide a coating having a thickness of between about 1 and 5 mm. and preferably between 2 and 3 mm.

The presence of plasma at the surface wound area is important because it is the plasma fibrinogen and the thrombin located in the surface wound that react and ultimately result in the formation of fibrin which is replaced by fibroblasts required for the build-up of the new connective tissue thereby resulting in the rapid healing of the surface wound.

The source of plasma is preferably obtained from either a sample of blood from the patient or from the blood plasma flowing from the surface wound. The plasma may also result from a combination of the two sources.

When plasma is used from a blood sample already removed from the patient, it is desirable to obtain said plasma by taking 15 cc. of the patient's venous blood and mixing the same with 2.3 cc. of anticoagulant citrate dextrose and thereafter centrifuging at 2000 revolutions per minute for 10 minutes. The clear plasma is then collected in a sterile test tube for its subsequent use.

Plasma obtained in this manner, or by other conventional procedures, may be either used immediately in the practice of this invention or may be stored for future use, such as in a refrigerator, with conventional additives optionally being incorporated into the plasma to aid in the preservation thereof, which need not be removed for the subsequent use of the plasma in the practice of this invention.

When the compositions are applied over the surface wound, it is preferred to cover the entire surface wound although it is possible to promote the build-up of new connective tissue when at least a major portion of the surface wound has been coated. By major portion it is meant that at least 50 percent of the surface wound has been coated with the composition defined herein.

What is claimed is:

1. A method for promoting the growth of new connective tissue over a surface wound wherein at least a portion of the epithelium has been damaged or removed which comprises coating said wound with a composition consisting essentially of a connective tissue promoting agent of pulverized absorbable gelatin sponge, wherein plasma is present at the situs of the wound, said composition being present in an amount sufficient to promote the production of new connective tissue over said surface wound.

2. The method of claim 1 which comprises coating at least a major portion of said wound.

3. The method of claim 2 wherein said composition contains from about 5 to 50 mg. of said pulverized absorbable gelatin sponge for each 0.3 to 0.5 cc of plasma.

4. The method of claim 2 wherein said composition further comprises from about 12.5 to 75 mg. of aminocaproic acid for each 0.3 to 0.5 cc. of plasma.

5. The method of claim 4 comprising from about 5 to 50 mg. of said pulverized absorbable gelatin sponge for each 0.3 to 0.5 cc. of plasma and from about 12.5 to 75 mg. of aminocaproic acid for each 0.3 to 0.5 cc. of plasma.

6. The method of claim 5 wherein said surface wound is contaminated and said composition further comprises at least one antibiotic agent incorporated therein.

7. The method of claim 6 wherein said composition is applied over said surface wound in an amount sufficient to provide a coating having a thickness of between about 1 to 5 mm.

8. The method of claim 6 wherein the thickness of said coating is between 2 to 3 mm.

9. The method of claim 6 wherein said composition further comprises between about 5 and 50 mg. of finely divided collagen for each 0.3 to 0.5 cc. of plasma.

10. The method of claim 1 wherein said composition further comprises a second connective tissue promoting agent selected from the group consisting of: (1) aminocaproic acid, (2) a compound of the formula: $4NH_2CH_2(CH_2)_4COOH \cdot CaX_2$ wherein X is chloride or bromide, and (3) mixtures thereof.

* * * * *